United States Patent
Frommert et al.

(10) Patent No.: US 10,832,423 B1
(45) Date of Patent: Nov. 10, 2020

(54) OPTIMIZING AN ATLAS

(71) Applicant: Brainlab AG, Munich (DE)

(72) Inventors: Mona Frommert, Munich (DE); Robert Lucht, Munich (DE); Andreas Blumhofer, Neubiberg (DE)

(73) Assignee: Brainlab AG, Munich (DE)

( * ) Notice: Subject to any disclaimer, the term of this patent is extended or adjusted under 35 U.S.C. 154(b) by 165 days.

(21) Appl. No.: 16/317,588

(22) PCT Filed: Jan. 8, 2018

(86) PCT No.: PCT/EP2018/050356
§ 371 (c)(1),
(2) Date: Jan. 14, 2019

(87) PCT Pub. No.: WO2019/134757
PCT Pub. Date: Jul. 11, 2019

(51) Int. Cl.
*G06T 7/33* (2017.01)
*G06T 7/00* (2017.01)
*G06T 5/50* (2006.01)

(52) U.S. Cl.
CPC ............... *G06T 7/344* (2017.01); *G06T 5/50* (2013.01); *G06T 7/0012* (2013.01); *G06T 2207/20221* (2013.01); *G06T 2207/30004* (2013.01)

(58) Field of Classification Search
CPC ......... G06T 7/344; G06T 7/0012; G06T 5/50; G06T 2207/10081; G06T 2207/10088;
(Continued)

(56) References Cited

U.S. PATENT DOCUMENTS 9,406,130 B2 * 8/2016 Vilsmeier ............ G16H 50/50
9,508,144 B2 * 11/2016 Vilsmeier ............ G16H 50/50
(Continued)

FOREIGN PATENT DOCUMENTS

EP  1991305 A1  11/2008
WO  2014/063745 A1  5/2014

OTHER PUBLICATIONS

European Patent Office, International Search Report and Written Opinion corresponding to PCT/EP2018/050356, dated Sep. 13, 2018, pp. 1-20.

*Primary Examiner* — Michael S Osinski
(74) *Attorney, Agent, or Firm* — Tucker Ellis LLP

(57) ABSTRACT

Disclosed is a computer-implemented method of determining an atlas element. The method encompasses acquiring model image data that describes at least one fixed element (an anatomical element such as an anatomical body part, for example, a rib). Patient image data is acquired that describes an improvable element (an anatomical element such as an anatomical body part, for example heart). Region data is acquired, for example by assigning a homogeneous grey value to a region of the model image. The patient image is matched to the model image, wherein no matching is performed within the region. A transformation for mapping the improvable element into the region is determined based on matching. Several patient images are then mapped into the region and superimposed. An atlas element is determined based on the superimposed images. The method may be repeated using the determined anatomical atlas element as a constraint to detect further atlas elements.

19 Claims, 7 Drawing Sheets

(58) Field of Classification Search
CPC . G06T 2207/30012; G06T 2207/10072; G06T 2207/30004; G06T 15/08; G06T 2210/41; A61B 5/055; A61B 5/0035; A61B 6/032; A61B 6/12; A61B 6/504; A61B 6/5223; A61B 6/5247; A61B 6/037; A61B 6/461; A61B 6/467; A61B 6/501–508; A61B 8/463; A61B 8/5246; G06F 19/321
See application file for complete search history.

(56) References Cited

U.S. PATENT DOCUMENTS

| | | | | |
|---|---|---|---|---|
| 10,417,762 | B2* | 9/2019 | Blumhofer | G06T 7/30 |
| 2005/0215854 | A1* | 9/2005 | Ozaki | A61B 1/00009 |
| | | | | 600/109 |
| 2009/0232378 | A1* | 9/2009 | Nakamura | G06T 7/337 |
| | | | | 382/131 |
| 2010/0150418 | A1* | 6/2010 | Moriya | G06T 19/00 |
| | | | | 382/128 |
| 2010/0286995 | A1* | 11/2010 | Pekar | G06T 7/12 |
| | | | | 705/2 |
| 2011/0032259 | A1* | 2/2011 | Kim | A61B 1/0005 |
| | | | | 345/428 |
| 2012/0155734 | A1* | 6/2012 | Barratt | G06T 7/344 |
| | | | | 382/131 |
| 2012/0163687 | A1* | 6/2012 | Plakas | G06T 7/38 |
| | | | | 382/131 |
| 2012/0314924 | A1* | 12/2012 | Carlton | G06K 9/6215 |
| | | | | 382/131 |
| 2013/0044927 | A1* | 2/2013 | Poole | G06T 7/0014 |
| | | | | 382/131 |
| 2013/0172727 | A1* | 7/2013 | Mori | G06K 9/42 |
| | | | | 600/407 |
| 2013/0194267 | A1* | 8/2013 | Tsujita | A61B 8/14 |
| | | | | 345/424 |
| 2014/0114633 | A1* | 4/2014 | Watanabe | G06T 19/20 |
| | | | | 703/11 |
| 2014/0133728 | A1* | 5/2014 | Blaffert | G06T 7/155 |
| | | | | 382/131 |
| 2014/0358114 | A1* | 12/2014 | Rosenbluth | G06F 19/3468 |
| | | | | 604/500 |
| 2015/0010223 | A1 | 1/2015 | Sapiro et al. | |
| 2015/0035829 | A1* | 2/2015 | Miyamoto | A61B 6/504 |
| | | | | 345/423 |
| 2015/0139520 | A1* | 5/2015 | Senegas | G06T 7/0014 |
| | | | | 382/131 |
| 2015/0173715 | A1* | 6/2015 | Raghavan | A61B 8/565 |
| | | | | 600/440 |
| 2015/0278471 | A1* | 10/2015 | Blumhofer | G16H 50/50 |
| | | | | 703/11 |
| 2015/0287198 | A1 | 10/2015 | Vilsmeier | |
| 2015/0287202 | A1* | 10/2015 | Wang | G06T 1/0007 |
| | | | | 382/128 |
| 2015/0363979 | A1* | 12/2015 | Takano | A61B 6/462 |
| | | | | 345/633 |
| 2016/0000299 | A1* | 1/2016 | Itai | A61B 1/31 |
| | | | | 600/103 |
| 2016/0191887 | A1* | 6/2016 | Casas | H04N 13/156 |
| | | | | 348/47 |
| 2016/0232655 | A1* | 8/2016 | Lachner | G06T 7/337 |
| 2016/0331262 | A1* | 11/2016 | Kuck | A61B 5/0464 |
| 2016/0358336 | A1 | 12/2016 | Franz et al. | |
| 2017/0042495 | A1* | 2/2017 | Matsuzaki | A61B 6/037 |
| 2017/0258393 | A1* | 9/2017 | Karino | G06T 7/174 |
| 2018/0005378 | A1* | 1/2018 | Varkuti | G06T 7/0016 |
| 2018/0008232 | A1* | 1/2018 | Mine | A61B 8/463 |
| 2018/0360342 | A1* | 12/2018 | Fuimaono | A61B 18/1492 |
| 2019/0105013 | A1* | 4/2019 | Wang | A61B 8/0858 |
| 2019/0214126 | A1* | 7/2019 | Goetz | A61B 34/10 |
| 2019/0251724 | A1* | 8/2019 | Schreckenberg | G06T 7/0012 |
| 2019/0350657 | A1* | 11/2019 | Tolkowsky | A61B 90/36 |
| 2020/0113450 | A1* | 4/2020 | Nishioka | A61B 5/02028 |
| 2020/0205749 | A1* | 7/2020 | Fukushima | A61B 8/485 |

\* cited by examiner

OPTIMIZING AN ATLAS

RELATED APPLICATION DATA

This application is a National Phase Application of International Application No. PCT/EP2018/050356 filed Jan. 8, 2018 and published in the English language.

FIELD OF THE INVENTION

The present invention relates to a computer-implemented method for determining atlas element data, a corresponding computer program, a non-transitory program storage medium storing such a program and a computer for executing the program, as well as a medical system comprising an electronic data storage device and the aforementioned computer.

TECHNICAL BACKGROUND

The present invention has the object of determining an atlas element using a model image and at least one patient image. The present invention can be used to improve an existing medical atlas, for example an anatomical atlas, for example a multimodal anatomical atlas of Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The disclosed method encompasses acquiring model image data which describes an image of at least one fixed element (e.g. an anatomical element such as an anatomical body part, for example a rib). The model image can be determined based on model data (e.g. atlas data). Patient image data is acquired which describes an image of an improvable element (e.g. an anatomical element such as an anatomical body part, for example a heart) of which an atlas element is to be determined. For example, the improvable element corresponds to an atlas element, which atlas element is to be improved (e.g. with spatial and/or representational properties of the atlas element which is to be determined). Next, region data is acquired, for example by assigning a homogeneous grey value to a given region of the model image, in which an anatomical element is expected to lie.

Subsequently, the patient image is matched to the model image (e.g. via elastic fusion), wherein no matching is performed within the region. Thereby, transformations of the fixed part between the patient image and the model image are obtained (described by model transformation data). Transformations for the improvable element of the patient image (which lies inside the region) are determined based on the obtained transformations described by the model transformation data.

Several patient images are then mapped into the region and superimposed. An atlas element is determined based on the superimposed images automatically or manually.

The method may then be repeated using an outline of the determined atlas element as a so-called revised region, i.e. using the determined anatomical atlas element as constraint to detect further atlas elements.

GENERAL DESCRIPTION OF THE INVENTION

In this section, a description of the general features of the present invention is given for example by referring to possible embodiments of the invention.

The invention relates to determining atlas element data. In general, the invention reaches the aforementioned object by providing, in a first aspect, a computer-implemented medical method of determining atlas element data describing an atlas element. The method comprises executing, on at least one processor of at least one computer (for example at least one computer being part of the medical system according to the fifth aspect described below), the following exemplary steps which are executed by the at least one processor. The singular form "a", "an" and "one" used in the current application and in the claims comprises the meaning of "at least one".

In a (for example first) exemplary step, model data is acquired. The model data for example describes a (e.g. at least one) fixed element. The (e.g. at least one) fixed element for example represents an (e.g. at least one) anatomical element such as an anatomical body part of a human (e.g. a bone, a muscle or else). The fixed element in another example represents at least a part of an anatomical element. For example, the anatomical element is a substructure of an anatomical body or an anatomical body part which can be distinguished from other substructures of the anatomical body or the anatomical body part. The model data is for example atlas data (i.e. describing an anatomical atlas) and for example describes a plurality of anatomical elements. The fixed element represents for example a landmark (see chapter "Definitions" below). The fixed element may represent (e.g. at least a part of) an artificial reference structure such as a marker, e.g. metal marker, isotopic marker or a radio-opaque marker. For example, the model data is (for example part of) an anatomic atlas. For example, the model data is based on a generic model of an anatomical body structure and/or an anatomical body part. For example, the model data describes a fixed element which is a generic model of an anatomical body structure and/or an anatomical body part.

For example, the model data describes the fixed element by specifying spatial and/or representational properties of the fixed element, e.g. separately from one another. That is, the spatial property can be used separately from the representational property. For example, the spatial property is stored as a separate entity from the representational property but is associated thereto (e.g. linked thereto, for example via an association table or metadata). For example, each pixel or voxel of the model image described below has a given representational property (e.g. image intensity value) and a given spatial property (e.g. size and position in a given reference system). The spatial property for example describes a position and/or geometry (shape and/or size) of the fixed element. In a general example, the representational property describes how the fixed element with a given spatial property is to be displayed using a display device. The representational property for example describes a grey value, a colour value, an image intensity value, an upper and/or lower limit of a grey value, a colour value and/or an image intensity value (and/or else) of the fixed element.

In a further (for example second) exemplary step, region data is acquired. For example, the region data describes a region. As noted above, the term "a" region also comprises the meaning "at least one" region, that is, the region data for example describes one or more than one region, for example a plurality of regions. For example, the region data is determined based on input made by a user, for example via a user input device such as a touch screen. For example, the region data describes a spatial property (for example a position and/or geometry (shape and/or size)) of the region and/or of an outline of the region. For example, the region data describes a shape representative. The outline is for example a virtual shape surrounding the whole region. For example, in the case of a three-dimensional region, the outline is the surface of the region. For example, in the case of a two-dimensional region, the outline is the border of the region designating which parts (e.g. of an image) belong to the region and which parts do not.

For example, an improvable element lies at least partially within the region described by the region data. For example, the improvable element represents an (e.g. at least one) anatomical element such as an anatomical body part of a human (e.g. a bone, a joint, a muscle, an organ, a part of an organ, a cluster of organs or a cluster of parts of organs). The improvable element in another example represents at least a part of an anatomical element. For example, the improvable element is an element of which an atlas element is to be determined. For example, the improvable element corresponds to an atlas element comprised in an anatomical atlas, which atlas and/or atlas element is to be improved as will be described below.

For example, the improvable element does not touch or intersect at least a part of an outer contour of the region. For example, the outer contour of the region is the outline of the region described above. For example, the improvable element touches at least a part of the outer contour of the region if the improvable element comprises one or more pixels or voxels, referred to as inside border pixels or voxels, which are comprised in the region and lie directly adjacent to one or more pixels or voxels, referred to as outside border pixels or voxels, which are not comprised in the region, but the improvable element does not comprise pixels or voxels which are not comprised in the region, wherein the at least a part of the outer contour of the region is defined by (e.g. is equal to) a border separating the inside border pixels or voxels from the outside border pixels or voxels. For example, the improvable element intersects at least a part of the outer contour of the region if the improvable element comprises one or more pixels or voxels, referred to as inside border pixels or voxels, which are comprised in the region and lie directly adjacent to one or more pixels or voxels, referred to as outside border pixels or voxels, which are not comprised in the region, and the improvable element also comprises at least some of the outside border pixels or voxels, wherein the at least a part of the outer contour of the region is defined by (e.g. is equal to) a border separating the inside border pixels or voxels from the outside border pixels or voxels.

For example, the fixed element (e.g. at least one fixed element or all fixed elements) lies (for example at least partially or completely) outside the region.

For example, the fixed element touches at least a part of an outer contour of the region. For example, the outer contour of the region is the outline of the region described above. For example, the fixed element touches at least a part of the outer contour which the improvable element does not touch or intersect. For example, the fixed element touches at least a part of the outer contour of the region if the fixed element comprises one or more pixels or voxels, referred to as outside border pixels or voxels, which are not comprised in the region and lie directly adjacent to one or more pixels or voxels, referred to as inside border pixels or voxels, which are comprised in the region, but the fixed element does not comprise pixels or voxels which are comprised in the region, wherein the at least a part of the outer contour of the region is defined by (e.g. is equal to) a border separating the inside border pixels or voxels from the outside border pixels or voxels.

For example, the region data describes a predetermined representational property of at least a part (e.g. all parts) of the region. In a general example, the representational property describes how the fixed element with a given spatial property is to be displayed using a display device. The representational property for example describes a grey value, a colour value, an image intensity value, an upper and/or lower limit of a grey value, a colour value and/or an image intensity value (and/or else) of (the at least a part of) the region. The representational property for example describes a value of a minimized image energy of the region which is for example lower than that of a matching image and/or of a patient image. The representational property for example describes a value of a spectral density of the region which is for example lower than that of a matching image and/or of a patient image. The representational property for example describes a value of an information content/of the region. The representational property for example describes a range of colour information of a certain colour depth (e.g. 1 bit, 8 bit, 32 bit, 256 bit), which range is for example lower than that of a matching image and/or of a patient image.

In a (for example third) exemplary step, model image data is determined. The model image data is for example two- or three-dimensional image data. The model image data is for example determined based on the model data and the region data. For example, the model image data describes at least one (two-dimensional or three-dimensional) image of at least a part of the fixed element and of at least a part of the region, the image being referred to as model image. For example, the spatial property of the fixed element and of the region is used to select a spatial range from the model image data from which to generate the model image. For example, the model image exhibits representational properties which are determined based on a representational property of the fixed element and/or of the region. For example, the at least a part of the region exhibits a predetermined representational property described by the model data. In another example, the at least a part of the region exhibits a predetermined representational property described by the region data.

As noted above, a two-dimensional or three-dimensional patient image can be used. Also, a two-dimensional or three-dimensional model image can be used. For example, in case a two-dimensional patient image is used, a two-dimensional model image is used. For example, in case a three-dimensional patient image is used, a three-dimensional model image is used. For example, the model image has the same imaging modality as the patient image. For example, the patient image data is acquired before the model image data is determined and the model image data is determined so that the model image has the same imaging modality as the patient image. For example, the imaging modality of the model image is not identical to the imaging modality of the patient image, but the model image is sufficiently similar to the patient image, wherein it is determined whether the model image is sufficiently similar to the patient image based on an image similarity measure (i.e. (average) of image intensity, resolution, image size or else).

In a (for example fourth) exemplary step, patient image data is acquired. The patient image data is for example two-dimensional or three-dimensional image data. For example, the patient image data describes an image of a corresponding improvable element and of a (e.g. of at least one) corresponding fixed element, the image being referred to as patient image. The term "corresponding" as used here for the "corresponding" improvable element and for the "corresponding" fixed element in both cases refers to an anatomical correspondence and means in particular "anatomically the same", in particular "representing the same anatomical element" or "representing the same anatomical body part" which can be seen as a part of a patient's body which is present in a plurality of different patient's bodies and in particular belongs to the same representation class(es) (see below for the definition of representation class) and/or consists of the same material and/or is located at least approximately at the same location relative to other anatomical elements and/or has a similar geometry (size and/or shape) in a plurality of different patients. For example, the corresponding improvable element represents an anatomical element which is the same as (e.g. is exactly identical to) the anatomical element represented by the improvable element. That is, there is for example a bijective (one-to-one) assignment between the corresponding improvable element and the improvable element and between the corresponding fixed element and the fixed element. In another example, there is a surjective assignment between the corresponding improvable element and the improvable element and between the corresponding fixed element and the fixed element.

In a further (for example fifth) exemplary step, model transformation data is determined. For example, the model transformation data is determined based on the model image data and the patient image data. For example, the model transformation data is determined based on the model image data, the patient image data and the region data. For example, the model transformation data describes a transformation for matching the corresponding fixed element to the fixed element. For example, the model transformation data describes a transformation for matching the corresponding fixed element to the fixed element but not the region. For example, the transformation is determined by rigidly or elastically fusing a patient image with a model image. For example, the transformation is determined by rigidly or elastically fusing only parts of the patient image with only parts of the model image. For example, the transformation comprises several transformations for several different pixels or voxels comprised in the corresponding fixed element, for example for all pixels or voxels comprised in the corresponding fixed element.

For example, the transformation (e.g. the model transformation) comprises a spatial transformation which only acts on the spatial property and not on the representational property of the patient image data and/or the model image data, i.e. which only processes spatial information (e.g. the spatial property) but not representational information (e.g. the representational property). The same is true for the "transformations" and "mappings" described below, i.e. the transformations and the mappings comprise transformations which only describe spatial transformations, for example in the form of a transformation matrix describing a spatial shift and/or spatial deformation, for example a spatial rotation or else. A transformed image is for example determined by two distinct steps. According to one step, the spatial transformation is applied to an image, whereby the spatial properties are transformed using the transformation. According to another step, the representational properties which are for example linked to the spatial properties as noted above can be assigned to the transformed spatial properties, thereby obtaining the transformed image including transformed spatial properties and the linked representational properties. Performing the two steps is an example of performing a transformation (e.g. a model transformation). The steps can be performed in arbitrary sequence or in parallel.

In a further (for example sixth) exemplary step, region transformation data is determined. For example, the region transformation data is determined (at least or only) based on the model transformation data. For example, the region transformation data describes a transformation for mapping the corresponding improvable element into the region. For example, the corresponding improvable element is mapped into a part of the region, i.e. does not fill out the complete region after the mapping.

There are at least two possible ways to determine the region transformation data, both of which are covered by the wording of originally filed claim 1. The first way will be described below as example A, whilst the second way will be described below as option B. These two ways may also be combined as far as possible to determine the region transformation data.

Example A

In example A, the transformation for mapping the corresponding improvable element into the region is determined by performing the following steps of example A. For example, the model image data in example A describes the image of the at least a part of the fixed element and of the at least a part of the region, wherein the at least a part of the region exhibits a predetermined representational property described by the region data (as discussed in detail above).

In a (for example first) exemplary step of example A, patient transformation data is determined. For example, the patient transformation data is determined based on the patient image data and the model image data. For example, the patient transformation data describes a transformation for matching the corresponding improvable element to a part of the matching image which lies within the region. For example, an (e.g. elastic or rigid) image fusion is performed between a part of the patient image including the corresponding improvable element and a part of the matching image which lies within the region. For example, an image fusion is performed between the whole patient image and the whole matching image, wherein the at least a part of the region in the matching image exhibits a predetermined representational property, and the transformations of pixels or voxels within the region obtained by the image fusion are described by the patient transformation data.

In most cases, a matching between the part of the patient image including the corresponding improvable element and the part of the matching image which lies within the region is not possible, for example in case no representational and/or structural feature is present in the part of the matching image which lies within the region which could be matched to the corresponding improvable element. This is due to the fact that the at least a part of the region exhibits the predetermined representational property described by the region data as laid out in detail above. In general, for a matching between images to be possible, both images need to comprise a minimum amount of image information. In example A, the predetermined representational property described by the region data is chosen such that no or only a certain number (i.e. a numerical number below an acquired predetermined threshold) transformations can be obtained by matching the part of the patient image including the corresponding improvable element and the part of the matching image which lies within the region. For choosing the predetermined representational property, the patient image is for example analysed beforehand, determining a representational property of the patient image. Afterwards, the predetermined representational property is for example chosen so as to be lower than the determined representational property of the patient image, for example lower by (a) predetermined value(s).

In case a matching between the part of the patient image including the corresponding improvable element and the part of the matching image which lies within the region is not possible, the patient transformation data for example describes a predetermined transformation referred to as empty transformation.

In a (for example second) exemplary step of example A, transformation field data is determined. The transformation field data is for example determined based on the model transformation data and the patient transformation data. For example, the transformation field data describes a transformation field specifying at least a part of the transformations described by the model transformation data and at least a part of the transformations described by the patient transformation data. For example, the transformation field comprises transformations for some or all of the pixels or voxels included in the patient image data and/or in the model image data, i.e. not just for the pixels or voxels within the region but also for the pixels or voxels outside the region.

In a (for example third) exemplary step of example A, approximated transformation field data is determined. For example, the approximated transformation field data is determined based on the transformation field data. For example, the approximated transformation field data describes an approximated transformation field which is determined by approximating the transformation field for the region. For example, the approximating comprises at least one of interpolating, extrapolating or model-fitting. For example, the approximating is performed using predetermined approximation constraints such as for example at least one threshold for a deviation between transformations of two adjacent pixels or voxels of the patient image. For example, the empty transformations which are comprised in the transformation field are not used for approximating, i.e. some or all of the transformations comprised in the transformation field are used for determining the approximated transformation field, whilst the empty transformations are not used for determining the approximated transformation field. In this example, the approximated transformation field comprises some or all of the transformations of the transformation field which are not empty transformations. For example, the empty transformations comprised in the transformation field are assigned other values by the approximation. In this example, the approximated transformation field comprises some or all of the transformations of the transformation field which are not empty transformations and also comprises the assigned other values of the empty transformations. That is, the approximation for example approximates values of transformations for pixels or voxels for which the transformation field contains either no or an empty transformation. In other words, the approximation for example interpolates the transformation field using all transformations as fixed points (boundary conditions for the approximation) whilst assigning new values to the pixels or voxels for which the transformation field contains either no or an empty transformation.

In a (for example fourth) exemplary step of example A, the transformation for mapping the corresponding improvable element into the region is determined based on the approximated transformation field. For example, the transformation for mapping the corresponding improvable element comprises several transformations for several different pixels or voxels comprised in the corresponding improvable element, for example for all pixels or voxels comprised in the corresponding improvable element.

Example B

In example B, the transformation for mapping the corresponding improvable element into the region is determined by performing the following steps of example B. For example, the model image data in example B describes the image of the at least a part of the fixed element and of the at least a part of the region, wherein the at least a part of the region does or does not exhibit a predetermined representational property described by the region data.

In a (for example first) exemplary step of example B, transformation field data is determined. For example, the transformation field data is determined based on the model transformation data. For example, the transformation field data describes a transformation field specifying at least a part of the transformations described by the model transformation data. For example, the transformation field data describes a transformation field specifying only at least a part of the transformations described by the model transformation data, i.e. does not describe any transformations described by the patient transformation data described above under "Example A". That is, in contrast to example A, in example B the transformation field data for example does not describe any transformations for pixels or voxels (of the patient image or the model image) which lie within the region. As explained above, in example A, for example a predetermined representational property is assigned to the region so that no or only a certain number of transformations described by the patient transformation data can be determined based on the matching, i.e. most or all of the pixels or voxels within the region are assigned an empty transformation. In contrast thereto, in example B the region may exhibit any representational property and a matching between the corresponding improvable element to a part of the matching image which lies within the region may result in not only the certain number of, but in many (i.e. in more than the certain number of) (non-empty) transformations. That is, an image fusion between a part of the patient image including the corresponding improvable element and a part of the model image including the region is for example possible in example B since the region of the model image does not exhibit the predetermined representational property, but for example includes an image of the improvable element. Nevertheless, these transformations for pixels or voxels within the region are for example discarded in example B by determining the transformation field only based on the model transformation data and not based on the patient transformation data.

In a (for example second) exemplary step of example B, interpolated transformation field data is determined. For example, the interpolated transformation field data is determined based on the transformation field data. For example, the interpolated transformation field data describes an interpolated transformation field. The interpolated transformation field is for example determined by interpolating the transformation field for the region. For example, the interpolating comprises at least one of interpolating, extrapolating or model-fitting. For example, the interpolating is performed using predetermined interpolation constraints such as for example at least one threshold for a deviation between transformations of two adjacent pixels or voxels of the patient image. For example, any transformations which are not described by the transformation field data are not used for interpolating, i.e. some or all of the transformations comprised in the transformation field described by the transformation field data are used for determining the interpolated transformation field, whilst any other (e.g. empty) transformations are not used for determining the interpolated transformation field. In this example, the interpolated transformation field comprises some or all of the transformations of the transformation field described by the transformation field data. For example, any pixels or voxels (of the patient image or of the model image) within the region are assigned specific transformations by the interpolation. In this example, the interpolated transformation field comprises some or all of the transformations of the transformation field described by the transformation field data and also comprises the assigned specific transformations. That is, the interpolation for example interpolated values of transformations for pixels or voxels for which the transformation field described by the transformation field data contains no transformation. In other words, the interpolation for example interpolates the transformation field using all given transformations as fixed points (boundary conditions for the interpolation) whilst assigning specific transformations to the pixels or voxels for which the transformation field contains no transformation.

In a (for example third) exemplary step of example B, the transformation for mapping the corresponding improvable element into the region is determined based on the interpolated transformation field. For example, the transformation for mapping the corresponding improvable element comprises several transformations for several different pixels or voxels comprised in the corresponding improvable element, for example for all pixels or voxels comprised in the corresponding improvable element.

In the following, the description of the method according to the first aspect is continued, for example following the step of determining the transformation for mapping the corresponding improvable element into the region.

In a further (for example seventh) exemplary step, atlas element data is determined. For example, the atlas data is determined based on the patient image data and the region transformation data. For example, the atlas element data describes an atlas element representing the improvable element. The term "representing" means that the properties of the atlas element are for example not exactly identical with an anatomical body part of a single patient, for example in case a plurality of patient images is used for determining the atlas element. For example, the atlas element describes a generic model of the improvable element, i.e. a generic model of an anatomical element. For example, the atlas element data specifies a shape representative (see chapter "Definitions" below). For example, the atlas element data describes the atlas element by specifying spatial and/or representational properties of the atlas element separately from one another. That is, the spatial property can be used separately from the representational property. For example, the spatial property is stored as a separate entity from the representational property but is associated thereto (e.g. linked thereto, for example via an association table or metadata). The spatial property for example describes a position and/or geometry (shape and/or size) of the atlas element. In a general example, the representational property describes how the atlas element with a given spatial property is to be displayed using a display device. The representational property for example describes a grey value, a colour value, an image intensity value, an upper and/or lower limit of a grey value, a colour value and/or an image intensity value (and/or else) of the atlas element.

For example, the atlas element data describes the atlas element by specifying further properties of the atlas element, e.g. separately from the aforementioned properties. For example, the atlas element data specifies a representation class of the atlas element, an anatomical tissue class, a weight, a density, movement information (e.g. relative movement with respect to other anatomical body parts) or else. For example, atlas data is used to determined one or more of the properties specified by the atlas element data, for example by matching the determined atlas element to a corresponding atlas element of an atlas and by assigning properties of the corresponding atlas element of the atlas to the determined atlas element.

For example, the determined atlas element data is used to improve an existing (e.g. medical and/or anatomical and/or multi-modal) atlas. The atlas for example describes a generic model of a plurality of anatomical elements, the elements in the generic model being referred to as atlas elements. The atlas for example describes a generic model of an anatomical body structure. For example, the atlas is improved by adding the determined atlas element as an additional atlas element to the existing atlas, thereby increasing the amount of atlas elements comprised in the atlas. For example, the atlas is improved by adding the determined atlas element as a substructure to an anatomical element comprised in the atlas, thereby increasing the resolution of the atlas. For example, the determined atlas element is matched with a corresponding atlas element comprised in the atlas, whereby the anatomical atlas (e.g. described by atlas data) can be improved, part by part, by improving the spatial property of some of the atlas elements (in particular at least one atlas element, for example the corresponding atlas element) and/or by improving the representational property of at least said at least one atlas element. The term "corresponding" as used here has the same meaning as described above with respect to the corresponding improvable element and the corresponding fixed element, mutatis mutandis.

For example, the atlas element is added to the model data, for example using the properties of the atlas element such as shape, position and representation. For example, the atlas element replaces a corresponding element described by the model data. For example, the atlas element and the corresponding element described by the model data are used to determine an averaged new atlas element which replaces the corresponding element. For this purpose, some or all of the properties of the atlas element and of the corresponding element described by the model data are for example averaged (weighted, mode, mean or else). For example, the model data comprising the atlas element is used as an atlas.

For example, the region transformation data individually describes the transformation for each of a plurality of patient images described by the patient image data, the transformation being referred to as individual transformation. That is, there is for example a separate transformation for each of the plurality of patient images and all of these transformations are described by the region transformation data. For example, the atlas element data is determined by performing at least the following exemplary steps A to C.

In a first exemplary step A, transformed patient image data is determined. For example, the transformed patient image data is determined based on the patient image data and the region transformation data. For example, the transformed patient image data describes a plurality of images, for example of one or more patients. For example, the (plurality of) images described by the transformed patient image data are determined by applying the individual transformation to each of the plurality of patient images, for example at least to parts of the plurality of patient images which lie within the region. For example, each image described by the transformed patient image data comprises the corresponding improvable element which has been transformed into the region using the individual transformation. For example, each image described by the transformed patient image data for comprises (i.e. describes, shows, represents) a transformed corresponding improvable element.

In a second exemplary step B, approximation image data is determined. For example, the approximation image data is determined based on the transformed patient image data. For example, the approximation image data describes an image referred to as approximation image. For example, the approximation image data describes an image obtained by superimposing at least parts of the plurality of images described by the transformed patient image data which lie within the region. For example, the superposition of the images is determined by combining representational properties of the images such as image intensity values, grey values or else. For example, the superposition is determined by summation, weighted averaging, mode averaging, mean averaging, or else of the representational properties of the images. For example, the superposition includes a normalization step. For example, the image described by the approximation image data comprises (i.e. describes, shows, represents) an average of some or all of the transformed corresponding improvable elements.

In a third exemplary step C, the atlas element data is determined based on the approximation image data. For example, not only a single patient image is used to determine the atlas element data, but a plurality of patient images are used to determine an approximation image which is subsequently used to determine the atlas element data.

For example, the atlas element data is determined by performing at least the following exemplary steps D to F, which for example follow the aforementioned exemplary steps A to C.

In a first exemplary step D, distinction data is acquired. For example, the distinction data describes a property of an image of an anatomical element.

For example, the distinction data describes at least one of the following:
  i. at least one representational property,
  ii. at least one threshold (e.g. a minimum and/or maximum threshold) describing a numerical image intensity value, for example a grey value,
  iii. at least one threshold (e.g. minimum and/or maximum threshold) for example describing a numerical image brightness value and/or describing a threshold of relative image intensity,
  iv. at least one spatial property (for example a position and/or geometry (shape and/or size)),
  v. at least one structural pattern describing a (e.g. typical) structure in an image of at least a part of an anatomical element.

Some or all of the above (i. to v.) are for example described for the image modality of the patient image and/or the model image. Some or all of the above (i. to v.) are for example determined based on at least one patient image. Some or all of the above (i. to v.) are for example determined using machine learning (e.g. a deep learning algorithm). Some or all of the above (i. to v.) may be specific for a given representation class and/or tissue class. The distinction data for example comprises some or all of the aforementioned (i. to v.) for different image modalities.

In an exemplary second step E, element designation data is determined. For example, the element designation data is determined based on the element approximation data and the distinction data. For example, the element designation data describes parts of the approximation image (which image is described by the approximation image data), which parts exhibit the property described by the distinction data. For example, the element designation data describes a selection region (two-dimensional or three-dimensional) within the approximation image which comprises at least a part of the corresponding improvable element, wherein the parts of the approximation image within the selection region exhibit the property described by the distinction data.

In an exemplary third step F, the atlas element data is determined based on the element designation data. For example, the spatial property of the atlas element is determined based on the selection region, for example identical to the selection region. For example, the representational property of the atlas element is determined based on the representational properties of parts of the approximation image which lie inside the selection region.

Instead or in addition to the exemplary steps A to C and/or D to F, the atlas element data is for example determined by performing at least the following exemplary steps G to I.

In a first exemplary step G, the image described by the approximation image data (the approximation image) is displayed on a display device. The display device is, for example, a computer screen, an augmented reality device such as augmented reality glasses, a light projection device or else. For example, the approximation image is displayed in combination with a marking of the outline of the region and/or the selection region.

In a second exemplary step H, element selection data is acquired describing parts of the image displayed on the display device. For example, the element selection data describes a second selection region which comprises a part of the approximation image. For example, the second selection region is determined by a used, for example based on the displayed image. For example, the element selection data is determined based on user input, for example user input on a touchscreen or via a user interface.

In a third exemplary step I, the atlas element data is determined based on the element selection data. For example, the spatial property of the atlas element is determined based on the second selection region, for example identical to the second selection region. For example, the representational property of the atlas element is determined based on the representational properties of parts of the approximation image which lie inside the second selection region.

Alternatively or additionally, the atlas element data is determined based on the selection region and also based on the second selection region. In this case, an averaging of the second selection region and of the selection region is for example performed to determine a final selection region and the atlas element data is determined based on the final selection region. For example, the selection region is determined after acquiring the second selection region. In this case, the distinction data is for example determined based on the spatial and/or representational properties for the parts of the approximation image which lie within the second selection region. That is, the distinction data is for example used to refine the second selection region.

In this case, the atlas element data is for example determined based on the selection region which is determined based on the distinction data, wherein the distinction data is determined based on the second selection region.

In a further (for example eighth) exemplary step, atlas element property data is determined. For example, the atlas element property data is determined based on the atlas element data. For example, the atlas element property data describes a representational property of the atlas element. For example, the atlas element property data is determined by averaging a representational property of the atlas element.

In a further (for example ninth) exemplary step, representation class data is acquired. For example, the representation class data describes a representational property of an anatomical element belonging to a certain representation class. A representation class for example comprises elements which exhibit a given representational property. For example, a representation class is defined by a range of image intensity values. For example, a representation class is defined by at least one of the points i. to v. described above for the distinction data. For example, a representation class corresponds to an anatomical tissue class. For example, a representation class is generated as described in publication WO 2014/064063.

In a further (for example tenth) exemplary step, assignment data is determined. For example, the assignment data is determined based on the atlas element property data and the representation class data. For example, the assignment data describes whether the representational property of the atlas element corresponds to the representational property of the anatomical element belonging to the certain representation class. For example, the assignment data describes whether the representational property of the anatomical element fulfils at least one of the points i. to v. described above with respect to the distinction data, which points define a representation class.

In a further (for example eleventh) exemplary step, the atlas element data is assigned a certain representation class based on the assignment data. For example, in case the assignment data describes that the representational property of the anatomical element fulfils at least one of the points i. to v. described above with respect to the distinction data, which points define a representation class "X", the atlas element data is assigned the representation class "X". In case the representation class "X" corresponds to an anatomical tissue class "Y", the atlas element is for example assigned the representation class "X" and/or the anatomical tissue class "Y".

In a further exemplary step performed after determining the atlas element, revised model data is determined. For example, the revised model data is determined based on the acquired model data and the determined atlas element. For example, the revised model data describes at least parts of the model data which lie within the region but not within the determined atlas element. For example, the revised model data describes the fixed element and additional elements which lie within the region but outside the determined atlas element, which additional elements are used as fixed elements when repeating the method.

In a further exemplary step performed after determining the atlas element, revised region data is determined. For example, the revised region data is determined based on the acquired region data and the determined atlas element. For example, the revised region data describes parts of the region described by the acquired region data in which the determined atlas element lies. For example, the parts of the region in which the determined atlas element does not lie are excluded from the region described by the acquired region data so as to determine the region described by the revised region data. For example, the revised region data is determined based on an outline of the determined anatomical element, for example set to be identical with this outline.

In a further exemplary step performed after determining the revised model data and the revised region data, the method is repeated starting with the third exemplary step (i.e. without performing the first and the second exemplary step again), using the revised region data instead of the acquired region data, using the region described by the revised region data instead of the region described by the acquired region data, using the revised model data instead of the acquired model data and using the determined atlas element as a fixed element, for example as a further fixed element in addition to the fixed element described by the model data.

In other words, the method is for example repeated to determine at least one additional atlas element. For example, the at least one additional atlas element represents an additional improvable element. For example, for determining the additional atlas element, the determined atlas elements is used as a constraint, for example by using the outline of the determined atlas element as revised region. For example, the method is repeated until no additional atlas elements can be determined and/or until all determined atlas elements completely fill the region.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, carrying information which represents the program, for example the aforementioned program, which for example comprises code means which are adapted to perform any or all of the steps of the method according to the first aspect. A computer program stored on a disc is a data file, and when the file is read out and transmitted it becomes a data stream for example in the form of a (physical, for example electrical, for example technically generated) signal. The signal can be implemented as the signal wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention according to the second aspect therefore may alternatively or additionally relate to a data stream representative of the aforementioned program.

In a third aspect, the invention is directed to a non-transitory computer-readable program storage medium on which the program according to the fourth aspect is stored.

In a fourth aspect, the invention is directed to at least one computer (for example, a computer), comprising at least one processor (for example, a processor) and at least one memory (for example, a memory), wherein the program according to the second aspect is running on the processor or is loaded into the memory, or wherein the at least one computer comprises the computer-readable program storage medium according to the third aspect.

In a fifth aspect, the invention is directed to a medical system, comprising:
- the at least one computer according to the fourth aspect;
- an (i.e. at least one) electronic data storage device storing (at least) the model image data; and
- a medical imaging device for acquiring an image of a patient to generate the patient image data, wherein the at least one computer is operably coupled to the electronic data storage device for acquiring, from the data storage device, the model data and to the medical imaging device for acquiring, from the medical imaging device, the patient image data.

In an example of the system according to the fifth aspect, the medical device comprises a display device. The at least one computer is then operably coupled to the display device for transmitting, to the display device, control information so that the display device displays an image described by the approximation image data.

In an example of the system according to the fifth aspect, the medical device comprises a user input device. The at least one computer is then operably coupled to the user input device for acquiring, from the user input device, the element selection data.

For example, the invention does not involve or in particular comprise or encompass an invasive step which would represent a substantial physical interference with the body requiring professional medical expertise to be carried out and entailing a substantial health risk even when carried out with the required professional care and expertise.

More particularly, the invention does not involve or in particular comprise or encompass any surgical or therapeutic activity. The invention is instead directed as applicable to acquiring model data, patient image data and determining an atlas element. For this reason alone, no surgical or therapeutic activity and in particular no surgical or therapeutic step is necessitated or implied by carrying out the invention.

The present invention also relates to the use of the device/system or any embodiment thereof for determining an atlas element and/or improving an existing atlas with a determined atlas element. The use comprises for example at least one of the following steps:
- inputting information on a user input device so as to determine the region data which is for example subsequently acquired according to the method of the first aspect;
- acquiring an image of a patient so as to determine the patient image data which is for example subsequently acquired according to the method of the first aspect; and
- inputting information on a user input device so as to determine the element selection data which is for example subsequently acquired according to the method of the first aspect.

Definitions

In this section, definitions for specific terminology used in this disclosure are offered which also form part of the present disclosure.

Computer Implemented Method

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods such as for example medical imaging devices), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Acquiring Data

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Landmarks

A landmark is a defined element of an anatomical body part which is always identical or recurs with a high degree of similarity in the same anatomical body part of multiple patients. Typical landmarks are for example the epicondyles of a femoral bone or the tips of the transverse processes and/or dorsal process of a vertebra. The points (main points or auxiliary points) can represent such landmarks. A landmark which lies on (for example on the surface of) a characteristic anatomical structure of the body part can also represent said structure. The landmark can represent the anatomical structure as a whole or only a point or part of it. A landmark can also for example lie on the anatomical structure, which is for example a prominent structure. An example of such an anatomical structure is the posterior aspect of the iliac crest. Another example of a landmark is one defined by the rim of the acetabulum, for instance by the center of said rim. In another example, a landmark represents the bottom or deepest point of an acetabulum, which is derived from a multitude of detection points. Thus, one landmark can for example represent a multitude of detection points. As mentioned above, a landmark can represent an anatomical characteristic which is defined on the basis of a characteristic structure of the body part. Additionally, a landmark can also represent an anatomical characteristic defined by a relative movement of two body parts, such as the rotational center of the femur when moved relative to the acetabulum.

Shape Representatives

Shape representatives represent a characteristic aspect of the shape of an anatomical structure. Examples of shape representatives include straight lines, planes and geometric figures. Geometric figures can be one-dimensional such as for example axes or circular arcs, two-dimensional such as for example polygons and circles, or three-dimensional such as for example cuboids, cylinders and spheres. The relative position between the shape representatives can be described in reference systems, for example by co-ordinates or vectors, or can be described by geometric variables such as for example length, angle, area, volume and proportions. The characteristic aspects which are represented by the shape representatives are for example symmetry properties which are represented for example by a plane of symmetry. Another example of a characteristic aspect is the direction of extension of the anatomical structure, which is for example represented by a longitudinal axis. Another example of a characteristic aspect is the cross-sectional shape of an anatomical structure, which is for example represented by an ellipse. Another example of a characteristic aspect is the surface shape of a part of the anatomical structure, which is for example represented by a plane or a hemisphere. For example, the characteristic aspect constitutes an abstraction of the actual shape or an abstraction of a property of the actual shape (such as for example its symmetry properties or longitudinal extension). The shape representative for example represents this abstraction.

Atlas/Atlas Segmentation

Preferably, atlas data is acquired which describes (for example defines, more particularly represents and/or is) a general three-dimensional shape of at least one anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises image information (for example, positional image information) which can be matched (for example by applying an elastic or rigid image fusion algorithm) for example to image information (for example, positional image information) contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

For example, the atlas data includes information of the anatomical body part. This information is for example at least one of patient-specific, non-patient-specific, indication-specific or non-indication-specific. The atlas data therefore describes for example at least one of a patient-specific, non-patient-specific, indication-specific or non-indication-specific atlas. For example, the atlas data includes movement information indicating a degree of freedom of movement of the anatomical body part with respect to a given reference (e.g. another anatomical body part).

Medical Imaging Device

Medical imaging device are for example x-ray devices, CT devices or MRT devices which are used to generate analytical images (such as x-ray images or MRT images) of the body. For example, medical imaging devices are constituted to perform medical imaging methods. Medical imaging devices for example use medical imaging methods and are for example devices for analysing a patient's body, for instance by using waves and/or radiation and/or energy beams, for example electromagnetic waves and/or radiation, ultrasound waves and/or particles beams. Medical imaging devices are for example devices which generate images (for example, two-dimensional or three-dimensional images) of the patient's body (and for example of internal structures and/or anatomical parts of the patient's body) by analysing the body. Medical imaging devices are for example used in medical diagnosis, for example in radiology.

Imaging Methods

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data" or, in case is is generated on the basis of a patient, "patient image data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Matching

Matching describes a transformation (for example, linear transformation) of an element (for example, a pixel or voxel), for example the position of an element, of a first data set in a first coordinate system to an element (for example, a pixel or voxel), for example the position of an element, of a second data set in a second coordinate system (which may have a basis which is different from the basis of the first coordinate system). In one embodiment, the matching is determined by comparing (for example, matching) the color values (for example grey values) of the respective elements by means of an elastic or rigid fusion algorithm. The matching is embodied for example by a transformation matrix (such as a matrix defining an affine transformation).

Elastic Fusion, Image Fusion/Morphing, Rigid

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
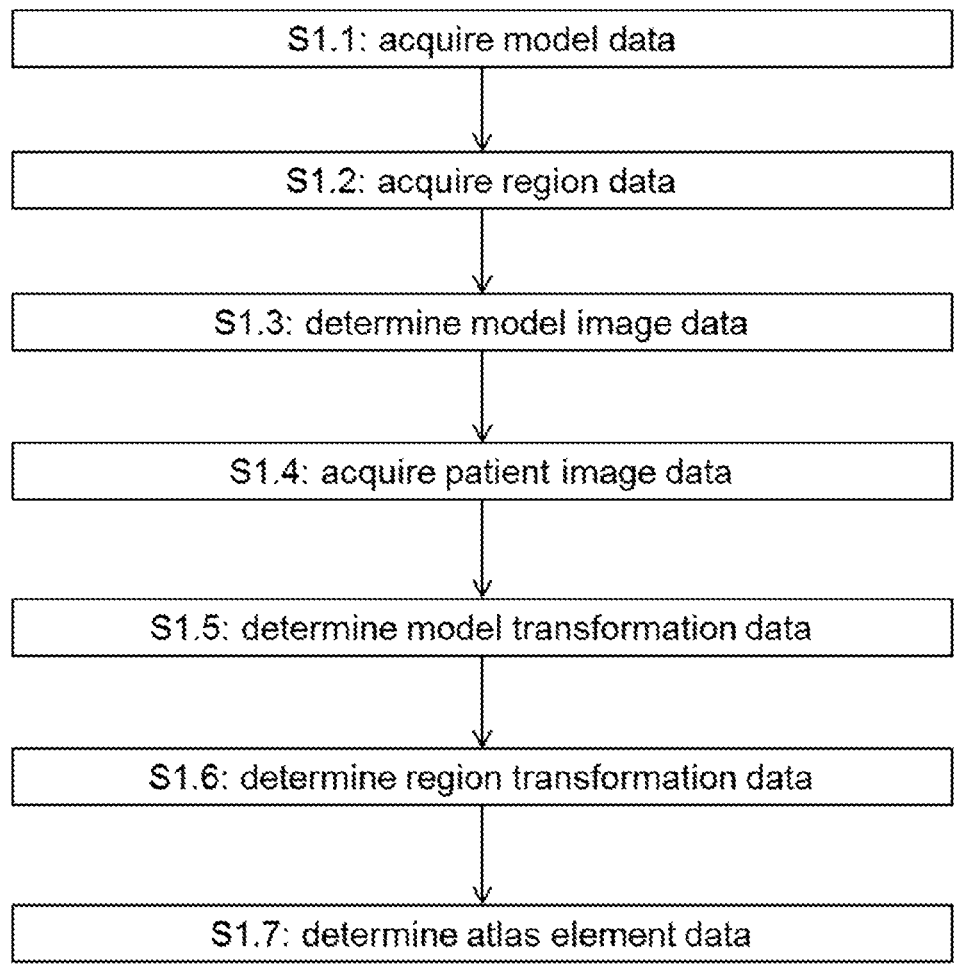
FIG. 1 illustrates a diagram of the method according to the first aspect.

FIG. 1 illustrates the basic steps of the method according to the first aspect, in which step S1.1 encompasses acquiring the model data, step S1.2 encompasses acquiring the region data, step S1.3 encompasses determining the model image data, step S1.4 encompasses acquiring the patient image data, step S1.5 encompasses determining the model transformation data, step S1.6 encompasses determining the region transformation data and step S1.7 encompasses determining the atlas element data.

Figure 2:
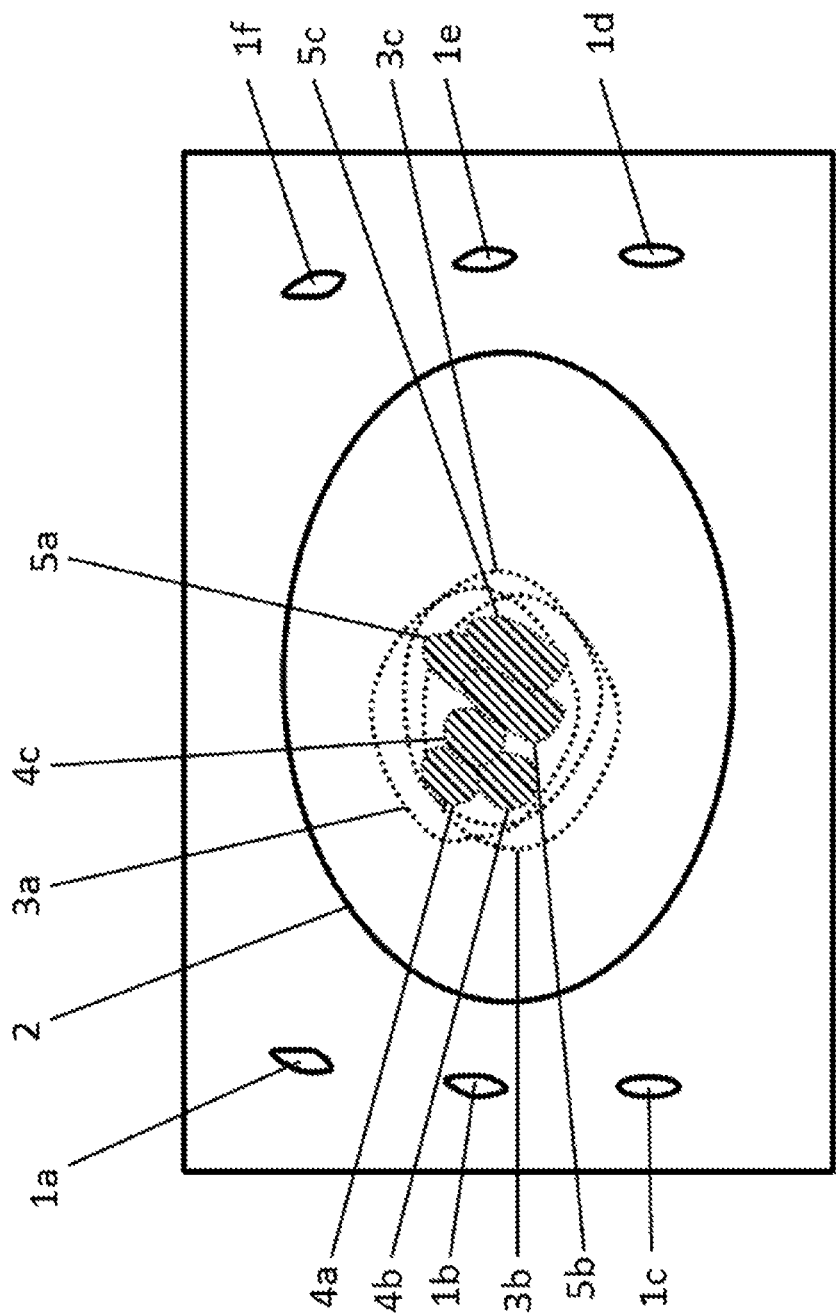
FIG. 2 shows an image including the outline of the region, the fixed elements and the approximation image according to the first aspect.

FIG. 2 shows an image including the outline 2 of the region, the fixed elements 1a to 1f and the approximation image according to the first aspect. The image shown in FIG. 2 comprises fixed elements 1a to 1f which for example represent bones (e.g. ribs). The outline of the region is denoted with reference sign 2. In this example, two-dimensional image data is used and a two-dimensional region can be described by its outline 2. Three patient images are matched to the matching image, for example only to parts of the image shown in FIG. 2 which lie outside the outline 2 of the region.

As described above, at least two options are possible to obtain the mapping of the corresponding improvable element of the patient image into the region: either the region is assigned a predetermined representational property (e.g. a homogeneous grey value), or the determined transformations for parts within the region are discarded before determining the interpolated transformation field. That is, for the mapping of the corresponding improvable element contained in the patient images, only matching information of pixels or voxels which lies outside the region is taken into account. Using the transformations determined for the image areas which lie outside the outline 2 of the region as boundary conditions, transformations for pixels or voxels within the outline 2 can be determined by approximation and/or interpolation as described above in example A and example B.

Subsequently, the parts of the patient images which lie within the region are mapped to the region and superimposed to obtain the approximation image. In FIG. 2, the approximation image is shown inside the outline 2 and includes, of each patient image, a large structure 3a to 3c and two small structures 4a to 4c and 5a to 5c, respectively.

Figure 3:
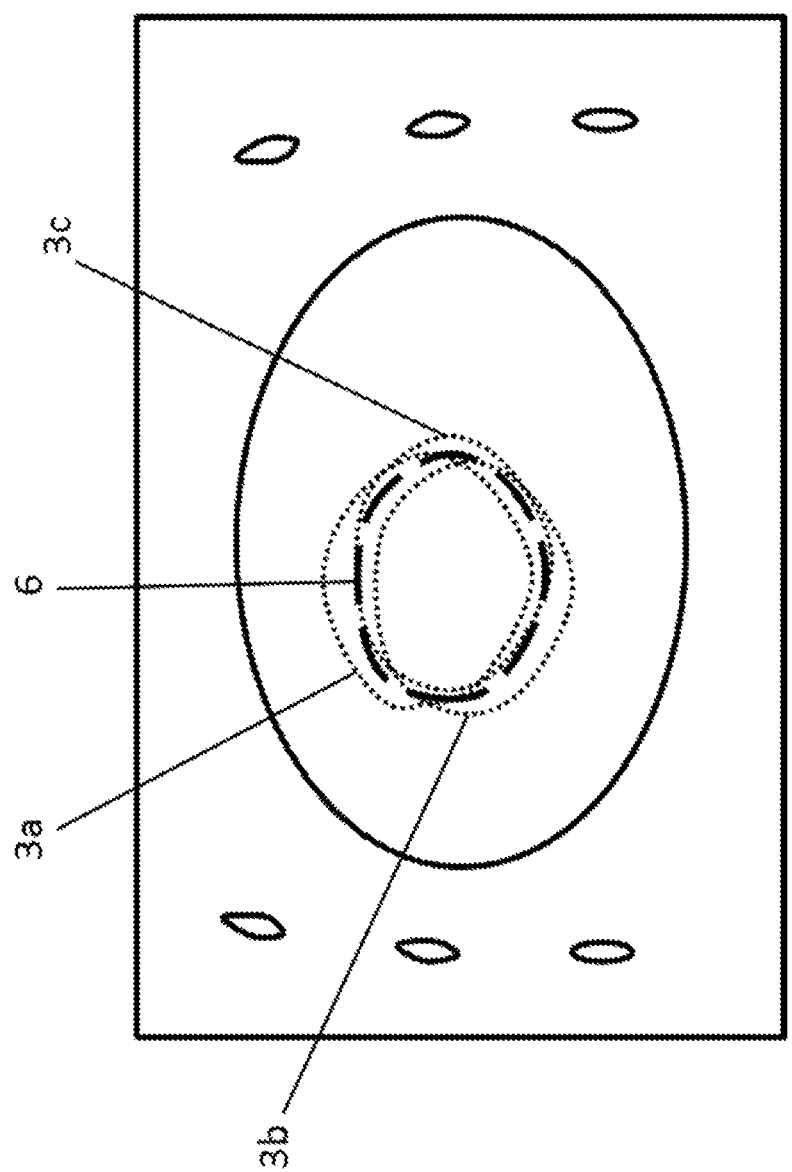
FIG. 3 shows an image including the outline of the region, the fixed elements, the approximation image and the selection region according to the first aspect.

FIG. 3 shows an image including the outline 2 of the region, the fixed elements 1a to 1f (shown without reference signs), the approximation image (shown without the small structures 4a to 4c and 5a to 5c) and the selection region 6 according to the first aspect. In this figure, only the large structures 3a to 3c of the approximation image are shown. The outline 6 of the selection region is determined as described above in accordance with the method according to the first aspect. For example, a given threshold for grey values (e.g. described by the distinction data) is used to segment a geometry of which the outline is used as the outline 6 of the selection region. Alternatively or additionally, as described above, a manual user selection can be used. The element which lies within the outline 6 of the selection region is for example determined as the atlas element.

Figure 4:
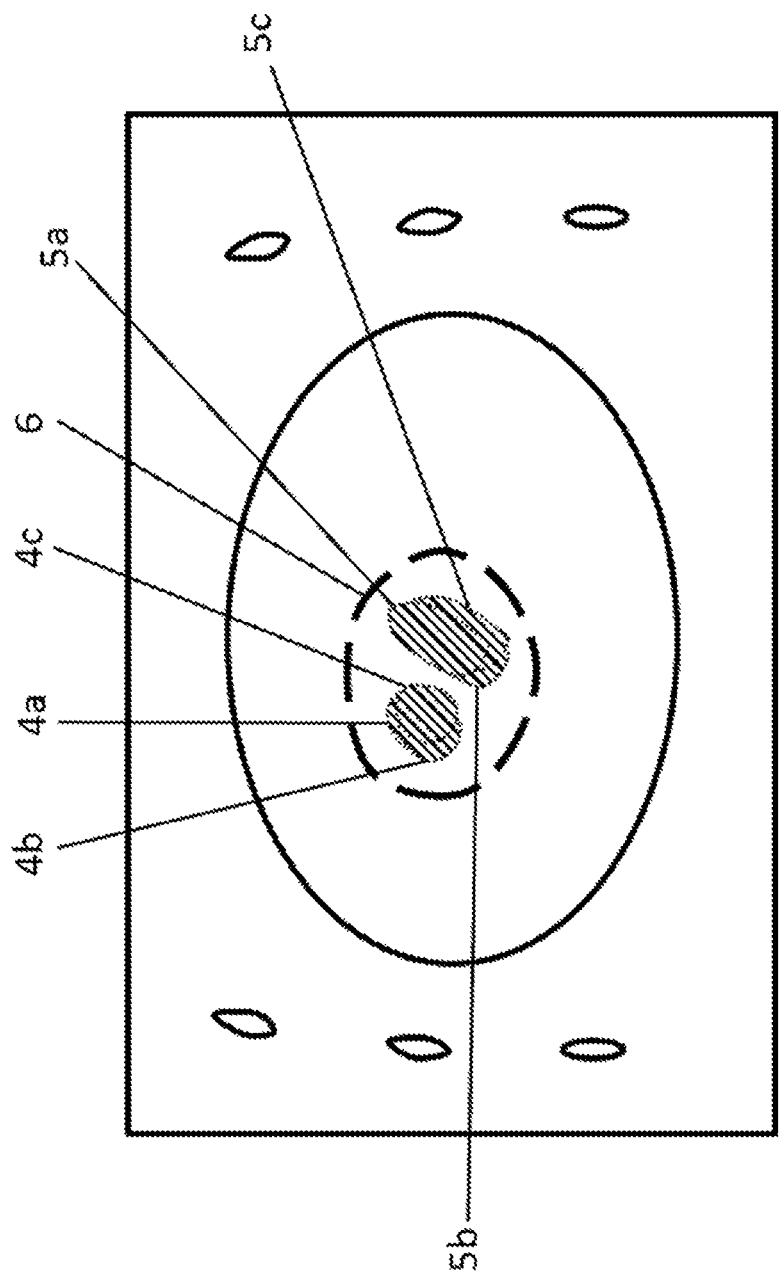
FIG. 4 shows an image including the outline of the region, the outline of the revised region and the approximation image according to the first aspect.
Figure 5:
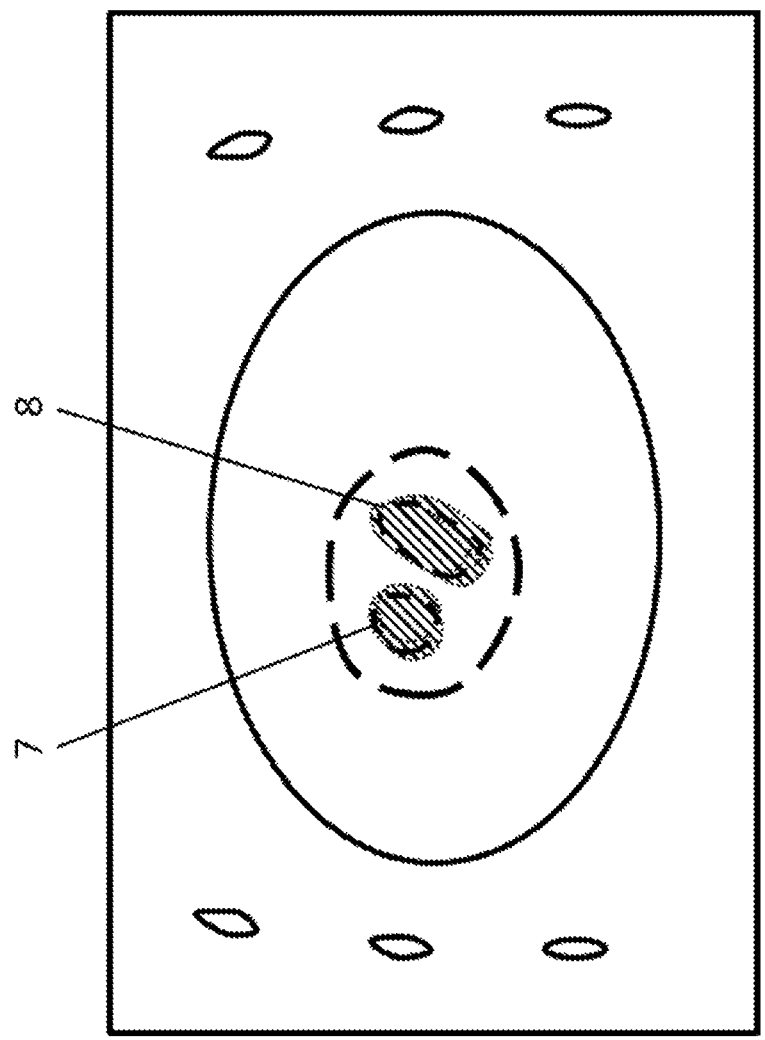
FIG. 5 shows an image including the outline of the region, the outline of the revised region, the approximation image and the selection region according to the first aspect.

Subsequently, the method may be repeated as described above. This is shown in FIG. 4 and FIG. 5. In particular, FIG. 4 shows an image including the outline 2 of the region, the outline of the revised region (which in this example is identical with the outline of the selection region 6 and also with the outline of the determined atlas element) and the new approximation image. The new approximation image is determined like the earlier approximation image—however, the revised model data and the revise region data are used That is, for determining the model transformation, all elements which lie outside the revised region are used as fixed elements. In this example, not only the fixed elements 1*a* to 1*f* noted above are used, but also all other elements which lie outside the revised region, including any elements which lie inside the region but outside the revised region. The transformation for mapping the (additional) corresponding improvable elements into the revised region is determined by interpolation and/or approximation as described above, whilst there are more support points for the interpolation in this case since there are more determined transformations available (the revised region is smaller than the region). This results in a refinement and in the detection of additional atlas elements.

FIG. 5 shows the image of FIG. 4, further including the detected additional atlas elements which are described by the outlines 7 and 8. Also in this case, the atlas elements may be determined using distinction data and/or user input. Also in this case, the outlines 7 and 8 may be used as outlines of revised regions for a subsequent repetition of the method. That is, the method may be repeated multiple times, using more fixed elements and (a) smaller revised region(s) for each iteration. This results in a refinement of the detected atlas elements. For example, the additional atlas elements are determined as belonging to the atlas element which was determined in the previous iteration and which outline surrounds the additional atlas elements.

Figure 6:
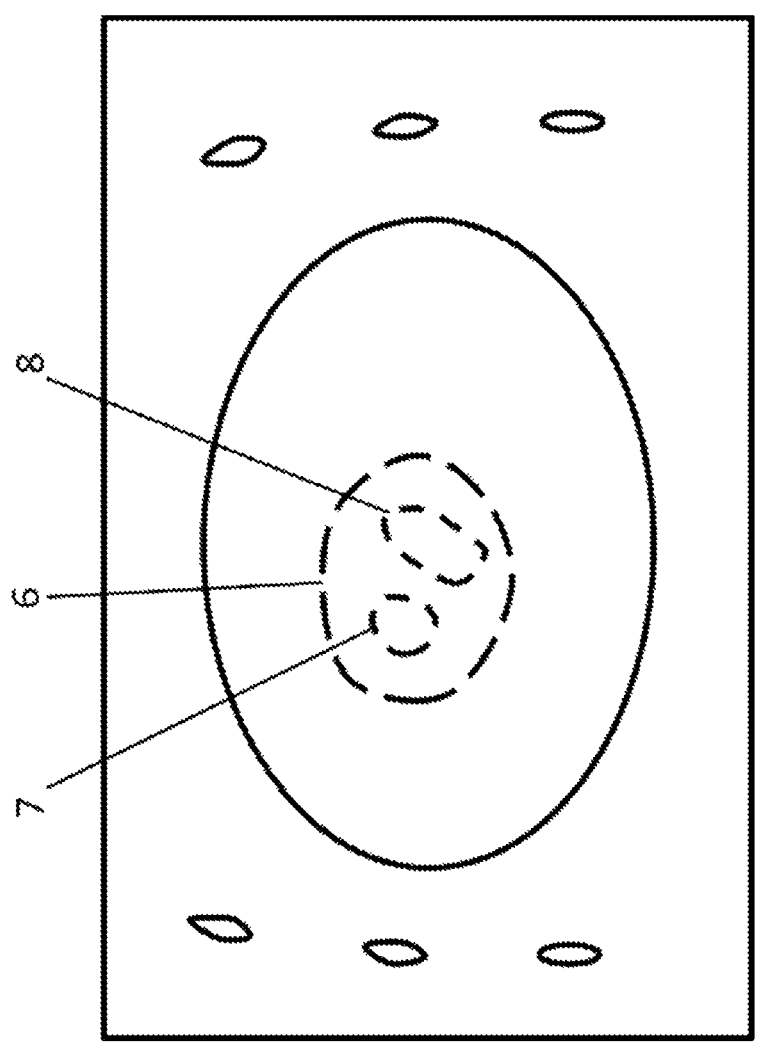
FIG. 6 shows an image including the determined atlas elements according to the first aspect.

FIG. 6 shows an image including the determined atlas elements according to the first aspect. In this example, the atlas element is described by the outline 6 and the additional atlas elements are described by the outlines 7 and 8, respectively. It should be noted that FIG. 6 shows only the spatial properties of the atlas elements which may be stored independently from representational information such as grey values of pixels.

Figure 7:
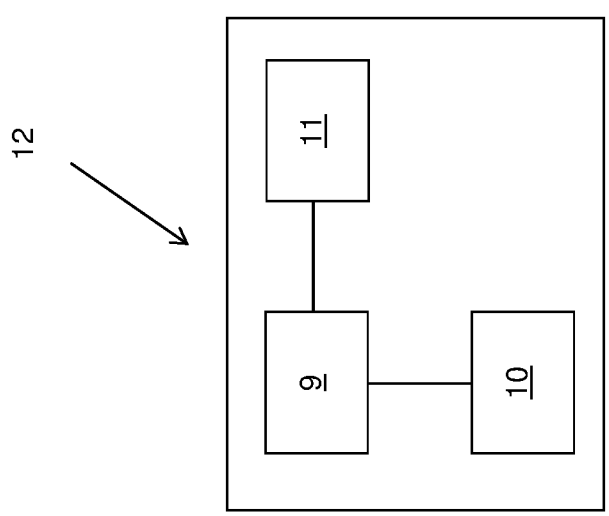
FIG. 7 shows is a schematic illustration of the system according to the fifth aspect.

FIG. 7 is a schematic illustration of the medical system 12 according to the fifth aspect. The system is in its entirety identified by reference sign 12 and comprises a computer 9, an electronic data storage device (such as a hard disc) 10 for storing at least the patient data and a medical imaging device 11. The medical imaging device 11 may be replaced by a display device or a user input device. Alternatively, the system further comprises the display device and/or the user input device. The components of the medical system 12 have the functionalities and properties explained above with regard to the fifth aspect of this disclosure.

The invention claimed is:

1. A computer-implemented medical method of determining atlas element data describing an atlas element, the method comprising the following steps:
    a) acquiring model data that describes a fixed element by specifying spatial and representational properties of the fixed element, the fixed element being a generic model of an anatomical body part, and the model data being atlas data of an anatomical atlas;
    b) acquiring region data that describes a region with an improvable element lying at least partially within the region, the improvable element representing an anatomical body part of which the atlas element data is to be determined, and the fixed element lying outside the region;
    c) determining model image data based on the model data and the region data, the model image data describing a model image of the fixed element and the region;
    d) acquiring patient image data describing a patient image of a corresponding improvable element and of a corresponding fixed element;
    e) determining, by rigidly or elastically fusing the patient image with the model image, model transformation data based on the model image data and the patient image data, the model transformation data describing a transformation for matching the corresponding fixed element to the fixed element;
    f) determining region transformation data based on the model transformation data, the region transformation data describing an individual transformation for mapping the corresponding improvable element into the region for each of a plurality of patient images described by the image data; and
    g) determining atlas element data based on the patient image data and the region transformation data, the atlas element data describing an atlas element representing the improvable element by specifying spatial and representational properties of the atlas element separately from one another, wherein the atlas element data is determined by performing at least the following steps:
        determining transformed patient image data based on the patient image data and the region transformation data, the transformed patient image data describing a plurality of images, the plurality of images being determined by applying the individual transformation to each of the plurality of patient images;
        determining approximation image data based on the transformed patient image data, the approximation image data describing an image obtained by superimposing at least parts of the plurality of images described by the transformed patient image data which lie within the region; and
        determining the atlas element data based on the approximation image data,
        wherein the spatial property of the fixed element describes a position and/or geometry of the fixed element, the representational property of the fixed element describes the manner in which the fixed element with a given spatial property is to be displayed, the spatial property of the atlas element describes a position and/or geometry of the atlas element, and the representational property of the atlas element describes how the atlas element with a given spatial property is to be displayed.

2. The method according to claim 1, wherein the model data describes the fixed element by specifying the spatial and the representational properties of the fixed element separately from one another.

3. The method according to claim 1, wherein the improvable element does not touch or intersect at least a part of an outer contour of the region.

4. The method according to claim 1, wherein the fixed element touches at least a part of an outer contour of the region.

5. The method according to claim 1, wherein the model image data describes the image of the fixed element and of the region,
wherein the region exhibits a predetermined representational property described by the region data.

6. The method according to claim 1, wherein the individual transformation for mapping the corresponding improvable element into the region for each of the plurality of the patient images described by the image data is determined by performing the following steps:
determining transformation field data based on the model transformation data, the transformation field data describing a transformation field specifying at least a part of the transformations described by the model transformation data;
determining interpolated transformation field data based on the transformation field data, the interpolated transformation field data describing an interpolated transformation field that is determined by interpolating the transformation field for the region; and
determining the individual transformation for mapping the corresponding improvable element into the region for each of the plurality of the patient images described by the image data based on the interpolated transformation field.

7. The method according to claim 1, wherein the atlas element data is determined by performing at least the following steps:
acquiring distinction data describing a property of an image of an anatomical element;
determining element designation data based on the element approximation data and the distinction data, the element designation data describing parts of the image, which image is described by the approximation image data, which parts exhibit the property described by the distinction data; and
determining the atlas element data based on the element designation data.

8. The method according to claim 7, wherein the distinction data describes at least one of the following:
at least one representational information;
at least one threshold describing a numerical image intensity value,
at least one threshold describing a numerical image brightness value,
at least one threshold describing a numerical image intensity value determined based on at least one patient image;
at least one threshold describing a numerical image brightness value determined based on at least one patient image;
at least one spatial information;
at least one structural pattern describing a typical structure in an image of at least a part of an anatomical element.

9. The method according to claim 1, wherein the atlas element data is determined by performing at least the following steps:
displaying the image described by the approximation image data on a display device;
acquiring element selection data describing parts of the image displayed on the display device; and
determining the atlas element data based on the element selection data.

10. The method according to claim 1, further comprising the following steps performed after determining the atlas element data:
determining atlas element property data based on the atlas element data, the atlas element property data describing a representational property of the atlas element;
acquiring representation class data describing a representational property of an anatomical element belonging to a certain representation class;
determining assignment data based on the atlas element property data and the representation class data, the assignment data describing whether the representational property of the atlas element corresponds to the representational property of the anatomical element belonging to the certain representation class; and
assigning the atlas element data a certain representation class based on the assignment data.

11. The method according to claim 1, wherein the method further comprises the following steps performed after determining the atlas element:
determining revised model data based on the acquired model data and the determined atlas element, the revised model data describing parts of the model data that lie within the region but not within the determined atlas element;
determining revised region data based on the acquired region data and the determined atlas element, the revised region data describing parts of the region described by the acquired region data in which the determined atlas element lies; and
repeating the method starting with step c), using the revised region data instead of the acquired region data, using the revised model data instead of the acquired model data, and using the determined atlas element as a fixed element.

12. A medical system, comprising:
at least one computer;
an electronic data storage device storing model image data; and
a medical imaging device for acquiring an image of a patient to generate patient image data,
wherein the at least one computer is operably coupled to the electronic data storage device for acquiring, from the data storage device, the model data, and to the medical imaging device for acquiring, from the medical imaging device, the patient image data, the computer being further configured to perform the following steps:
a) acquire model data that describes a fixed element by specifying spatial and representational properties of the fixed element, the fixed element being a generic model of an anatomical body part, and the model data being atlas data of an anatomical atlas;
b) acquire region data that describes a region with an improvable element lying at least partially within the region, the improvable element representing an anatomical body part of which the atlas element data is to be determined, and the fixed element lying outside the region;
c) determine model image data based on the model data and the region data, the model image data describing a model image of the fixed element and the region;
d) acquire patient image data describing a patient image of a corresponding improvable element and of a corresponding fixed element;
e) determine, by rigidly or elastically fusing the patient image with the model image, model transformation data based on the model image data and the patient image data, the model transformation data describing a transformation for matching the corresponding fixed element to the fixed element;

f) determine region transformation data based on the model transformation data, the region transformation data describing an individual transformation for mapping the corresponding improvable element into the region for each of a plurality of patient images described by the image data; and g) determine atlas element data based on the patient image data and the region transformation data, the atlas element data describing an atlas element representing the improvable element by specifying spatial and representational properties of the atlas element separately from one another, wherein the atlas element data is determined by performing at least the following steps:

determining transformed patient image data based on the patient image data and the region transformation data, the transformed patient image data describing a plurality of images, the plurality of images being determined by applying the individual transformation to each of the plurality of patient images;

determining approximation image data based on the transformed patient image data, the approximation image data describing an image obtained by superimposing at least parts of the plurality of images described by the transformed patient image data which lie within the region; and determining the atlas element data based on the approximation image data, wherein the spatial property of the fixed element describes a position and/or geometry of the fixed element, the representational property of the fixed element describes the manner in which the fixed element with a given spatial property is to be displayed, the spatial property of the atlas element describes a position and/or geometry of the atlas element, and the representational property of the atlas element describes how the atlas element with a given spatial property is to be displayed.

13. The system according to claim 12, wherein the individual transformation for mapping the corresponding improvable element into the region for each of the plurality of the patient images described by the image data is determined by:

determining transformation field data based on the model transformation data, the transformation field data describing a transformation field specifying at least a part of the transformations described by the model transformation data;

determining interpolated transformation field data based on the transformation field data, the interpolated transformation field data describing an interpolated transformation field that is determined by interpolating the transformation field for the region; and determining the individual transformation for mapping the corresponding improvable element into the region for each of the plurality of the patient images described by the image data based on the interpolated transformation field.

14. The system according to claim 12, wherein the atlas element data is determined by:

acquiring distinction data describing a property of an image of an anatomical element;

determining element designation data based on the element approximation data and the distinction data, the element designation data describing parts of the image, which image is described by the approximation image data, which parts exhibit the property described by the distinction data; and determining the atlas element data based on the element designation data.

15. The system according to claim 12, further comprising a display device, wherein the atlas element data is determined by:

displaying the image described by the approximation image data on the display device;

acquiring element selection data describing parts of the image displayed on the display device; and determining the atlas element data based on the element selection data.

16. The system according to claim 12, wherein the computer, after determining the atlas element data, is further configured to:

determine atlas element property data based on the atlas element data, wherein the atlas element property data describes a representational property of the atlas element;

acquire representation class data describing a representational property of an anatomical element belonging to a certain representation class;

determine assignment data based on the atlas element property data and the representation class data, wherein the assignment data describes whether the representational property of the atlas element corresponds to the representational property of the anatomical element belonging to the certain representation class;

assign the atlas element data a certain representation class based on the assignment data.

17. The system according to claim 12, wherein the computer, after determining the atlas element, is further configured to:

determine revised model data based on the acquired model data and the determined atlas element, the revised model data describing parts of the model data that lie within the region but not within the determined atlas element;

determine revised region data based on the acquired region data and the determined atlas element, the revised region data describing parts of the region described by the acquired region data in which the determined atlas element lies; and repeating the steps starting with step c), using the revised region data instead of the acquired region data, using the revised model data instead of the acquired model data and using the determined atlas element as a fixed element.

18. A non-transitory computer readable storage medium storing a computer program for determining atlas element data describing an atlas element, which, when running on a computer or loaded onto the computer, causes the computer to:

a) acquire model data that describes a fixed element by specifying spatial and representational properties of the fixed element, the fixed element being a generic model of an anatomical body part, and the model data being atlas data of an anatomical atlas;

b) acquire region data that describes a region with an improvable element lying at least partially within the region, the improvable element representing an anatomical body part of which the atlas element data is to be determined, and the fixed element lying outside the region;

c) determine model image data based on the model data and the region data, the model image data describing a model image of the fixed element and the region;

d) acquire patient image data describing a patient image of a corresponding improvable element and of a corresponding fixed element;

e) determine, by rigidly or elastically fusing the patient image with the model image, model transformation data based on the model image data and the patient image data, the model transformation data describing a transformation for matching the corresponding fixed element to the fixed element;

f) determine region transformation data based on the model transformation data, the region transformation data describing an individual transformation for mapping the corresponding improvable element into the region for each of a plurality of patient images described by the image data; and g) determine atlas element data based on the patient image data and the region transformation data, the atlas element data describing an atlas element representing the improvable element by specifying spatial and representational properties of the atlas element separately from one another, wherein the atlas element data is determined by:

determining transformed patient image data based on the patient image data and the region transformation data, the transformed patient image data describing a plurality of images, the plurality of images being determined by applying the individual transformation to each of the plurality of patient images;

determining approximation image data based on the transformed patient image data, the approximation image data describing an image obtained by superimposing at least parts of the plurality of images described by the transformed patient image data which lie within the region; and determining the atlas element data based on the approximation image data, wherein the spatial property of the fixed element describes a position and/or geometry of the fixed element, the representational property of the fixed element describes the manner in which the fixed element with a given spatial property is to be displayed, the spatial property of the atlas element describes a position and/or geometry of the atlas element, and the representational property of the atlas element describes how the atlas element with a given spatial property is to be displayed.

19. A computer comprising the non-transitory computer readable storage medium of claim 18.

* * * * *